United States Patent [19]
Grey

[11] Patent Number: 6,063,942
[45] Date of Patent: May 16, 2000

[54] CATALYST PREPARATION AND EPOXIDATION PROCESS

[75] Inventor: Roger A. Grey, West Chester, Pa.

[73] Assignee: Arco Chemical Technology, L.P., Greenville, Del.

[21] Appl. No.: 09/406,865

[22] Filed: Sep. 27, 1999

[51] Int. Cl.[7] ..................... C07D 301/03; C07D 301/06
[52] U.S. Cl. ............................... 549/523; 549/532
[58] Field of Search ...................... 549/523, 532

[56] References Cited

U.S. PATENT DOCUMENTS

| | | | |
|---|---|---|---|
| 5,744,619 | 4/1998 | Nemeth et al. | 549/523 |
| 5,780,654 | 7/1998 | Nemeth et al. | 549/531 |

FOREIGN PATENT DOCUMENTS

| | | |
|---|---|---|
| 19600709 | of 1997 | Germany . |
| 4-352771 | of 1992 | Japan . |
| 8-269029 | of 1996 | Japan . |
| 8-269030 | of 1996 | Japan . |
| WO 96/02323 | of 1996 | WIPO . |
| WO 97/25143 | of 1997 | WIPO . |
| WO 97/31711 | of 1997 | WIPO . |
| WO 97/47368 | of 1997 | WIPO . |

*Primary Examiner*—Amelia Owens
*Attorney, Agent, or Firm*—William C. Long

[57] ABSTRACT

An epoxidation catalyst is prepared by contacting a vanadium or titanium silicalite slurry with an ion exchangeable noble metal complex, and the catalyst is used without drying or calcining for olefin epoxidation by contact with $O_2$, $H_2$ and olefin.

6 Claims, No Drawings

CATALYST PREPARATION AND EPOXIDATION PROCESS

FIELD OF THE INVENTION

This invention relates to methods of oxidizing olefins to obtain epoxides. More particularly, this invention pertains to an improved epoxidation process wherein a titanium or vanadium zeolite catalyst which has been modified with a noble metal such as palladium is employed directly as prepared in the epoxidation without drying or calcining.

BACKGROUND OF THE INVENTION

Epoxides constitute an important class of -chemical intermediates useful for the preparation of polyether polyols, glycols, glycol ethers, surfactants, functional fluids, fuel additives and the like. Many different methods for synthesizing epoxides from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII noble metal and a crystalline titanosilicate. Improvements to or variations of this basic process were subsequently described in the following published patent applications: WO 97/25143, DE 19600709, WO 96/02323, WO 97/47386, WO 97/31711, JP H8-269030, and JP H8-269029.

As with any chemical process, it would be desirable to attain still further improvements in epoxidation methods of this type. In particular, increasing the ease of catalyst preparation and use would significantly enhance the commercial potential of such methods.

In the usual preparation of Group VIII metal modified zeolite catalysts, the Group VIII metal is added as a soluble compound solution to the solid zeolite particles and after an appropriate time the particles now containing the Group VIII metal are recovered, dried and calcined. Problems have existed as to the reproduceability of such procedures and the activity of the catalysts so-produced.

SUMMARY OF THE INVENTION

In accordance with the present invention, the Group VIII noble metal modified catalyst is prepared by mixing a solution of an ion exchangeable complex of the desired noble metal with a slurry of the titanium or vanadium silicalite in water or an organic solvent such as methanol. As a feature of the invention, the thusly formed catalyst is directly used in the epoxidation of an olefin with CO and hydrogen without complete solvent separation and drying and isolation of the catalyst as deemed necessary in the prior art; indeed improved epoxidation results are achieved through practice of the invention.

DETAILED DESCRIPTION OF THE INVENTION

The catalysts to be prepared and used in the present invention are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2 (1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent.

In accordance with the invention, the zeolite in particular form is slurried in a suitable solvent such as water or methanol or mixtures, and the noble metal is incorporated into the zeolite by contact with a solution containing a soluble compound of the noble metal, for example, aqueous Pd tetraammine chloride with or without added ammonium hydroxide. There are no particular restrictions other then solubility regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals.

Ambient temperatures are suitable for the catalyst preparation although higher or lower temperatures, eg. 0° C.–200° C., can be used. Generally the catalyst preparation is complete in an hour for so although longer or shorter times, eg. 5 minutes–5 hours can be used.

As a special feature of the invention, the slurry resulting from the catalyst preparation can be used directly for olefin epoxidation. For example, after completion of the catalyst preparation the temperature can be adjusted to the desired epoxidation temperature and oxygen, hydrogen and olefin reacted directly in the catalyst containing slurry to form epoxide. Epoxidation results achieved thereby can be better than those achieved by prior procedures where catalyst is dried and calcined before use.

While it is preferred to prepare fresh catalyst and use the catalyst directly in the epoxidation reaction, benefits can be achieved by adding the noble metal ion exchangable complex to a slurry which contains deactivated catalyst prepared by conventional procedures or by the procedures described above.

The olefin to be epoxidized can be any organic compound containing at least one site of ethylenic unsaturation (i.e., at least one carbon-carbon double bond). The olefin can be aliphatic, aromatic or cycloaliphatic in character and may have either a linear or branched structure, with the site(s) of ethylenic unsaturation being terminal and/or internal. The olefin preferably contains 2–30 carbon atoms; the process of the invention is particularly suitable for epoxidizing $C_2$–$C_6$ mono-olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro, groups or the like.

Typical examples of suitable olefins include ethylene, propylene, 1-butene, cis- and trans-2-butene, isobutene, 1,3-butadiene, pentenes, isoprene, hexenes, octenes, nonenes, decenes, undecenes, dodecenes, cyclopentene, cyclohexene, dicyclopentadiene, vinylcylohexane, vinyl cyclohexene, allyl chloride, allyl alcohol, methallyl chloride, methallyl alcohol, alkyl acrylates and methacrylates, unsaturated fatty acids and esters thereof, styrene, -methylstyrene, divinylbenzene, indene and stilbene. Mixtures of olefins may, of course, be utilized if so desired. The process of this invention is especially useful for converting propylene to propylene oxide.

The process of the invention may be suitably conducted under the reaction conditions (e.g., temperature, pressure, reactant ratios) described in the following published patent applications: WO 96/02323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin fed ratio of from 0.00001 to 0.1. The time required for the epoxidation may be determined on the basis of the gas hourly space velocity, i.e., the total volume of olefin, hydrogen, oxygen and carrier gas(es) per hour per unit of catalyst volume (abbreviated as GHSV). A GHSV in the range of 10 to 10,000 $hr^{-1}$ is typically satisfactory.

The epoxidation is carried out in the liquid phase, and it is advantageous to work at a pressure of 1–100 bars. Suitable solvents used in catalyst preparation and in the epoxidation include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water. Additional solvent can be added before or during epoxidation to improve process results.

Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2$=1:10 to 5:1 and is especially favorable at 1:5 to 2:1.

The molar ratio of oxygen to olefin is usually 1:1 to 1:20, and preferably 1:1.5 to 1:10. Relatively high $O_2$ to olefin molar ratios (e.g., 1:1 to 1:3) may be advantageous for certain olefins. As the carrier gas, any desired inert gas can be used. The molar ratio of olefin to carrier gas is then usually in the range of 1:100 to 4:1, and especially 20:1 to 1:1.

As the inert carrier gas, noble gases such as helium, neon, argon, krypton, and xenon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

Modifiers such as are described in co-pending applications Ser. No. 09/290,100 filed Apr. 12 1999, and Ser. No. 09/290,647 filed Apr. 12, 1999 can be used. The following examples further illustrate the invention and comparative procedures.

Comparative Example 1

Isolated Catalyst Preparation with Excess Ammonium Hydroxide

An Erlenmeyer flask equipped with a Teflon coated stir bar was charged with 20 grams of TS-1 titanium silicalite (1.5 wt % titanium, calcined in air at 550° C.) and 48 grams of deionized water. Palladium bromide (0.15 gram) was dissolved in 40 grams of 30% ammonium hydroxide and added to the silicalite slurry. The mixture was allowed to stir at 23° C. for 1 hr. and the liquid was removed by rotoevaporation at 50° C. The solids were dried in a vacuum oven at 55° C. (1 torr) for 2.5 hrs. The catalyst contained 0.5 wt % palladium.

Comparative Example 2

Isolated Catalyst with Lower Palladium Loading and Thermal Pretreatment

An Erlenmeyer flask equipped with a Teflon coated stir bar was charged with 30 grams of TS-1 titanium silicalite (1.2 wt % titanium, calcined in air at 550° C.) and 100 grams of deionized water. Palladium bromide (95 milligrams) was dissolved in 15 grams of 30% ammonium hydroxide and added to the silicalite slurry. The mixture was allowed to stir at 23° C. for 2 hrs. The liquid was removed by rotoevaporation at 50° C. The solids were dried in a vacuum oven (1 torr) at 50° C. for 4 hrs. The solids were then treated in a nitrogen stream (100 cc/min) at 120° C. for 4 hrs. The catalyst contained 0.12 wt % palladium.

Comparative Example 3

Isolated Catalyst with 0.5 wt % Palladium and Thermal Pretreatment

An Erlenmeyer flask equipped with a Teflon coated stir bar was charged with 30 grams of TS-1 titanium silicalite (1.2 wt % titanium, calcined in air at 550° C.) and 100 grams of deionized water. Palladium bromide (380 milligrams) was dissolved in 15 grams of 30% ammonium hydroxide and added to the silicalite slurry. The mixture was allowed to stir at 23° C. for 2 hrs. The liquid was removed by rotoevaporation at 50° C. The solids were dried in a vacuum oven (1 torr) at 50° C. for 4 hrs. The solids were then treated in a nitrogen stream (100 cc/min) at 120° C. for 4 hrs. The catalyst contained 0.48 wt % palladium.

Comparative Example 4

Isolated Catalyst with 0.5 wt % Palladium Made Without Excess Ammonium Hydroxide and No Thermal Pretreatment An Erlenmeyer flask equipped with a Teflon coated stir bar was charged with 30 grams of TS-1 titanium silicalite (1.2 wt % titanium, calcined in air at 550° C.) and 85 grams of deionizedwater. Tetraammino-palladium dibromide (480 mg) was dissolved in 30 grams of deionized water and added to the silicalite slurry over a 10 minute period. The mixture was allowed to stir at 23° C. for 2 hrs. The liquid was removed by rotoevaporation at 50° C. The solids were dried in a vacuum oven (1 torr) at 50° C. for 4 hrs. The catalyst contained 0.47 wt % palladium.

EXAMPLE 1

Water as the Solvent

Six grams of 30% aqueous ammonium hydroxide containing 41 mg of palladium bromide (enough to give 0.5 wt % palladium on the final catalyst) was added to 3 grams of TS-1 titanium silicalite (1.2 wt % titanium, calcined in air at 550° C.) slurried in 124 grams of deionized water in a glass reactor with a Teflon coated stir bar, under air atmosphere. After stirring at 23° C. for 60 minutes, the reactor was placed in constant temperature bath at 60° C. and $H_2$, $O_2$ and propylene bubbled through the slurry at about one atmosphere with stirring at 1000 rpm using a Teflon stir bar. The total flow of the feed was 112 cc/min with the $H_2:O_2:C_3$ volumetric ratio of 1:1:4, respectively, (O2=4 vol %) with nitrogen as the balance. Analysis of the vapor phase by GC showed 2700 ppm propylene oxide at the peak and a propylene oxide/propylene glycol=2. The catalyst produced 1900 ppm or greater of propylene oxide in the vapor for 40 hrs. A corresponding run using an analogous isolated catalyst prepared as in comparative example 1 gave 2200 ppm propylene oxide at the peak, produced 1900 ppm of propylene oxide or greater for 25 hrs and a propylene oxide/propylene glycol=1.6 for the run.

EXAMPLE 2

Methanol/Water as the Solvent Instead of Water Only

Palladium bromide (43 mg) was dissolved in 5.4 grams of deionized water containing 0.68 grams of 30% ammonium hydroxide. This solution, enough to give 0.5 wt % palladium on the final catalyst, was added to 3 grams of TS-1 titanium silicalite (1.2 wt % titanium, calcined 550° C.) slurried in a mixture of 22 grams of deionized water and 84 grams of methanol with a Teflon coated stir bar, under air atmosphere. After stirring at 23° C. for 2 hrs, the reactor was placed in a constant temperature bath at 45° C. and $H_2$, $O_2$ and propylene bubbled through the slurry at about one atmosphere with stirring at 1000 rpm using a Teflon stir bar. The total flow of the feed was 112 cc/min with the $H_2:O_2:C_3$ volumetric ratio of 1:1:4, respectively, (O2=4 vol %) with nitrogen as the balance. Analysis of the vapor phase by GC showed 2600 ppm propylene oxide at the peak and a ratio of propylene oxide/ring opened products=14 for the run. A corresponding run using an analogous isolated catalyst prepared as in comparative example 3 (but with a N2 pretreatment for 4 hrs at 150° C.) gave 2300 ppm propylene oxide at the peak and a ratio of propylene oxide/ring opened products=7.7 for the run.

EXAMPLE 3

Tetraammine Palladium Dichloride Without Ammonium Hydroxide as the Source of Palladium Tetraammine palladium dichloride (42 mg) was dissolved in 10 grams of deionized water. This solution, enough to give 0.5 wt % palladium on the final catalyst, was added to 3 grams of TS-1 titanium silicalite (1.2 wt % titanium) slurried in 120 grams of deionized water with a Teflon coated stir bar under an atmosphere of air. After stirring at 23° C. for 60 minutes, the reactor was placed in a constant temperature bath at 45° C. and $H_2$, $O_2$ and propylene bubbled through the slurry at about one atmosphere with stirring at 1000 rpm using a Teflon stir bar. The total flow of the feed was 112 cc/min with the $H_2:O_2:C_3$ volumetric ratio 1:1:4, respectively, (O2=4 vol %) with nitrogen as the balance. Analysis of the vapor phase by GC showed 2500 ppm propylene oxide at the peak and a propylene oxide/propylene glycol=3.3 for the run.

EXAMPLE 4

Addition of a Palladium Complex to a Deacitvated Catalyst During a Run

A reactor containing 3 grams of a 0.12 wt % Pd/TS-1 (prepared as in comparative example 2) in 130 grams of water was placed in a constant temperature bath at 60° C. and H2, O2 and propylene bubbled through the slurry at about one atmosphere with stirring of 1000 rpm using a Teflon stir bar. The total flow of the feed was 112 cc/min with the $H_2:O_2:C_3$ volumetric ratio of 1:1:4, respectively, (O2=4 vol %) with nitrogen as the balance. Analysis of the vapor phase by GC showed 2200 ppm propylene oxide at the peak at hour 10 and by hour 42 the propylene oxide in the vapor had declined to 400 ppm. At hour 42, 20 mg of tetraamine palladium dichloride dissolved in 10 grams of deionized water was added to the reaction mixture. By hr 58, the propylene oxide in the vapor had increased to 1300 ppm before beginning to slowly decline.

EXAMPLE 5

Addition of a Palladium Complex to Increase Propylene Oxide in the Vapor Before Deactivation A reactor containing 3 grams of a 0.48 wt % Pd/TS-1 (prepared as in comparative example 3) slurried in a mixture of 28 grams of water and 84 grams of methanol was placed in a constant temperature bath at 45° C. and $H_2$, $O_2$ and propylene bubbled through the slurry at about one atmosphere with stirring at 1000 rpm using a Teflon stir bar. The total flow of the feed was 112 cc/min with the $H_2:O_2:C_3$ volumetric ratio of 1:1:4, respectively, (O2=4 vol %) with nitrogen as the balance. Analysis of the vapor phase by GC showed a constant 2500 ppm of propylene oxide by hr 12. At hr 24, 40 mg of tetraammine palladium dichloride in 10 grams of methanol was added to the reaction mixture. By hr 54, the propylene oxide in the vapor had increased to a constant 2900 ppm.

EXAMPLE 6

Insitu Palladium Loading of a Previously Silylated Catalyst

A 250 mL Erlenmeyer flask equipped with a magnetic stir bar was charged with 37 grams of TS-1 titanium silicalite (titanium=1.2%, calcined at 550° C.) and 60 grams of toluene. To this slurry, 4 grams of BSTFA (bis(trimethylsilyl)trifluoroacetamide) in 5 grams of toluene was added over 5 minutes. The reaction mixture was stirred at 23° C. for 4 hrs. The solids were isolated by filtration, washed twice with 40 grams of toluene and dried in a vacuum oven (1 torr) at 40° C. for 2 hrs.

Tetraammine palladium dichloride (41 mg) was dissolved in 10 grams of deionized water. This solution, enough to give 0.5 wt % palladium on the final catalyst, was added to 3 grams of the previously trimethylsilylated TS-1 titanium silicalite (1.2 wt % titanium, calcined 550° C.) slurried in a mixture of 18 grams of deionized water and 84 grams of methanol with a Teflon coated stir bar under an air atmosphere. After stirring at 23° C. for 2 hrs, the reactor was placed in a constant temperature bath at 45° C. and $H_2$, $O_2$ and propylene bubbled through the slurry at about one atmosphere with stirring at 1000 rpm using a Teflon stir bar. The total flow of the feed is 112 cc/min with the $H_2:O_2:C_3$ volumetric ratio of 1:1:4 respectively, (O2=4 vol %) with nitrogen as the balance. Analysis of the vapor phase by GC showed a constant 3200 ppm propylene oxide by hr 38.

EXAMPLE 7

Run Analogous to Example 6 but the Catalyst is Silylated Last and Isolated

A 50 mL Erlenmeyer flask equipped with a magnetic stir bar was charged with 6 grams of palladium/TS-1 titanium silicalite (titanium=1.1 wt %), prepared as in comparative example 3, and 20 grams of toluene. To this slurry, one gram of BSTFA (bis(trimethylsilyl)trifluoroacetamide) in 5 grams of toluene was added over 5 minutes. The reaction mixture was stirred at 23° C. for 4 hrs. The solids were isolated by filtration, washed twice with 20 grams of toluene and dried in a vacuum oven (1 torr) at 40° C. for 2 hrs.

A reactor containing 3 grams of the 0.5 wt % Pd/Silylated TS-1 prepared above slurried in a mixture of 28 grams of water and 84 grams of methanol was placed in a constant temperature bath at 45° C. and $H_2$, $O_2$ and propylene bubbled through the slurry at about one atmosphere with stirring at 1000 rpm using a Teflon stir bar. The total flow of the feed is 112 cc/min with the $H_2:O_2:C_3$ volumetric ratio of 1:1:4 respectively, (O2=4 vol %) with nitrogen as the balance. Analysis of the vapor phase by GC showed constant 2400 ppm of propylene oxide by hr 12.

EXAMPLE 8

Use Tetraammine Palladium Dibromide without Ammonium Hydroxide as the Source of Palladium Tetraammine palladium dibromide (19 mg) was dissolved in 10 grams of deionized water. This solution, enough to 0.5 wt % palladium on the final catalyst, was added to 1 gram of TS-1 titanium silicalite (1.2 wt % titanium) slurried in 120 grams of deionized water with a Teflon coated stir bar under an air atmosphere. After stirring at 23° C. for 60 minutes, the reactor was placed in a constant temperature bath at 45° C. and $H_2$, $O_2$ and propylene bubbled through the slurry at about one atmosphere with stirring at 1000 rpm using a Teflon stir bar. The total flow of the feed is 112 cc/min with the $H_2:O_2:C_3$ volumetric ratio of 1:1:4 respectively, (O2=4 vol %) with nitrogen as the balance. Analysis of the vapor phase by GC showed 1900 ppm propylene oxide at the peak. An analogous run with one gram of catalyst where the catalyst was prepared according to comparative example 4 gave 1800 ppm propylene oxide at the peak. The ability to form active catalysts by this insitu procedure offers potential advantages for catalyst preparation in a commercial process.

I claim:

1. In a process for the epoxidation of an olefin by reaction of $O_2$, $H_2$ and olefin in contact with a noble metal containing titanium or vanadium silicalite, the improvement which comprises contacting a soluble ion exchangeable noble metal complex with solid titanium or vanadium silicalite slurried in a liquid solvent and without drying or calcining the resulting catalyst contacting the said catalyst with $O_2$, $H_2$ and olefin at reactive conditions.

2. In a process for the epoxidation of an olefin by reaction of $O_2$, $H_2$ and olefin in contact with a noble metal containing titanium or vanadium silicalite, the method of maintaining or restoring catalytic activity which comprises adding an ion exchangable complex of the noble metal to the reaction system.

3. The method of claim 1 wherein the olefin is propylene.

4. The method of claim 2 wherein the olefin is propylene.

5. The method of claim 1 wherein the noble metal is palladium.

6. The method of claim 2 wherein the noble metal is palladium.

* * * * *